US009719918B2

(12) United States Patent
Altendorf (10) Patent No.: US 9,719,918 B2
(45) Date of Patent: Aug. 1, 2017

(54) APPARATUS AND SYSTEM FOR DETERMINING, OPTIMIZING OR MONITORING AT LEAST ONE PROCESS VARIABLE

(71) Applicant: Endress + Hauser GmbH + Co. KG, Maulburg (DE)

(72) Inventor: Matthias Altendorf, Lorrach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 535 days.

(21) Appl. No.: 14/048,167

(22) Filed: Oct. 8, 2013

(65) Prior Publication Data
US 2014/0107940 A1 Apr. 17, 2014

(30) Foreign Application Priority Data
Oct. 11, 2012 (DE) .......................... 10 2012 109 680

(51) Int. Cl.
*G01N 21/35* (2014.01)
*G01N 21/3504* (2014.01)
*G01N 21/39* (2006.01)
*G01N 21/84* (2006.01)

(52) U.S. Cl.
CPC ......... *G01N 21/3504* (2013.01); *G01N 21/39* (2013.01); *G01N 2021/8411* (2013.01)

(58) Field of Classification Search
USPC .......................................................... 702/24
See application file for complete search history.

(56) References Cited

U.S. PATENT DOCUMENTS

| 5,839,094 | A  | 11/1998 | French |
| 7,440,735 | B2 | 10/2008 | Karschnia |
| 7,924,017 | B2 | 4/2011  | Ammann |
| 8,285,518 | B2 | 10/2012 | Babel |
| 8,612,920 | B2 | 12/2013 | Girardey |

(Continued)

OTHER PUBLICATIONS

Jack Driscoll (A Portable Gas Analyzer With Wireless Transmission of Gas Concentrations and GPS Coordinates. Posted: Apr. 2, 2010, 4 pages).*

(Continued)

*Primary Examiner* — Tung Lau
(74) *Attorney, Agent, or Firm* — Bacon & Thomas, PLLC (57) ABSTRACT

An apparatus for determining or monitoring at least one process variable, comprising: a sensor element and a measuring electronics, which form a measuring unit; and at least one control/evaluating/calculating unit arranged removed from the measuring unit; and/or an in/output unit arranged removed from the measuring unit and the control/evaluating/calculating unit. The control/evaluating/calculating unit and the in/output unit are connected with the measuring unit via a first interface and a second interface. The measuring electronics operates the sensor element and forwards the measurement signals via the interfaces to the control/evaluating/calculating unit as unprocessed, raw, measured values. The control/evaluating/calculating unit arranged removed from the measuring unit determines, improves and/or monitors the process variable based on the raw, measured values and makes such available via the in/output unit.

4 Claims, 4 Drawing Sheets

(56) References Cited

U.S. PATENT DOCUMENTS

2014/0012530 A1  1/2014  Reinhold
2014/0107940 A1  4/2014  Altendorf

OTHER PUBLICATIONS

Jack Driscoll, Portable Gas Analyzer with Wireless Transmission of Gas Concentrations and GPS Coordinates, Presented at the Pittsburgh Conference on Anal Chem . . . , Chicago, IL, Mar. 2007, 8 pages.*

Publication by I. Linnerud, et al., "Gas monitoring in the process industry using diode laser spectroscopy," 67 Appl. Phys. B 297 (1998).

* cited by examiner

APPARATUS AND SYSTEM FOR DETERMINING, OPTIMIZING OR MONITORING AT LEAST ONE PROCESS VARIABLE

TECHNICAL FIELD

The invention relates to an apparatus for determining, optimizing or monitoring at least one process variable. Furthermore, a system is presented, which, among other things, preferably comprises a plurality of the aforesaid apparatuses.

BACKGROUND DISCUSSION

In automation technology, especially in process automation, field devices are often applied, which serve for determining, optimizing and/or influencing process variables. Serving for registering process variables are sensors, such as, for example, gas sensors, gas analyzers, fill level measuring devices, flow measuring devices, pressure- and temperature measuring devices, pH-redox potential measuring devices, conductivity measuring devices, etc., which register the corresponding process variables, fill level, flow, pressure, temperature, gas quantities and gas qualities, pH-value, and conductivity. Serving for influencing process variables are actuators, such as, for example, valves or pumps, via which the flow of a liquid in a section of pipeline or the fill level in a container can be changed. Referred to as field devices are, in principle, all devices, which are applied near to the process and deliver or process information relevant to the process. In connection with the invention, field devices thus include also remote I/Os, radio adapters, or, generally, devices, which are arranged at the field level. A large number of such field devices are produced and sold by the firm, Endress+Hauser.

Known from European patent EP 1 629 331 A1 is a variable field device for process automation technology. The individual functions of this field device are distributed. The actual field device provides only a few basic functions, e.g. the measured value production, while application-specific functionalities, such as e.g. frequency- or pulse outputs, are embodied as separate functional units, which are arranged spatially separated from the field device. Field devices and functional units are connected to a corresponding communications medium for the purpose of data exchange. The communications medium is a two-conductor supply line. Alternatively, a number of data channels are provided on the communications medium, so that multiple access to the connected units is possible. In this way, the field device is variably and application-specifically configurable.

Known from German patent DE 10 2006 016 381 A1 is a measuring apparatus for determining and/or monitoring at least one process variable, wherein the measuring apparatus includes as integral components a sensor unit, an in/output unit and a display unit. The sensor unit produces raw, measured values, wherein from the raw, measured values the information concerning the process variable is producible. Data are received or forwarded via the in/output unit. Presented on the display unit is the information representing the process variable, as provided by a control unit. Communication between the sensor unit, the in/output unit and the display unit, on the one hand, and the control unit, on the other hand, occurs via one of the fieldbusses customary in automation technology.

In the field of gas analysis, reliable optical methods are applied, in the case of which light is led from a radiation source through a measuring chamber through which a gas mixture is flowing. Along this radiation path, certain specific gas component dependent absorptions of the light are effected and registered with a detector. From the amount of absorption of certain wavelengths of the light, the specific weight of individual components of the measured gas and their concentrations can be deduced. There are some known methods for measuring the gas concentrations, such as e.g. Non-Dispersive UltraViolet spectroscopy—NDUV, Non-Dispersive InfraRed spectroscopy—NDIR, as well as also laser absorption spectroscopy—TDLAS—Tunable Diode Laser Absorption Spectroscopy. Moreover, there are other methods, which will not be explored further here.

SUMMARY OF THE INVENTION

An object of the invention is to provide an apparatus and a system for determining, optimizing or monitoring at least one process variable simply and therewith cost effectively.

The apparatus of the invention includes the following components:

A measuring unit, respectively a measuring module, having a sensor element and measuring electronics;

at least one control/evaluating/calculating unit arranged removed from the measuring unit; and/or an in/output unit arranged removed from the measuring unit and the control/evaluating/calculating unit. The control/evaluating/calculating unit and/or the in/output unit communicate with the measuring apparatus of the invention via a first interface and a second interface. The measuring electronics operates the sensor element and forwards the measurement signals as unprocessed, raw, measured values via the interfaces to the control/evaluating/calculating unit.

Based on the raw, measured values, the control/evaluating/calculating unit arranged removed from the measuring unit determines, improves and/or monitors the process variable, which comprises at least one qualitative or quantitative, gas composition and/or gas concentration. Information concerning the process variable is made available via the in/output unit.

Integrated in the measuring unit are, thus, only the functional components necessarily required on-site for the measured value registering, such as, for instance, in the case of a fill-level measuring device, the signal producing unit and the transmitting- and receiving unit for the ultrasound- or microwave measurement signals. The conditioning- and further processing functions, same as the in- and output functions, are outsourced to a "central" control/evaluating/calculating unit, respectively a "central" in/output unit. The control/evaluating/calculating unit is preferably so embodied that the raw, measured values delivered from the most varied of measuring units can be conditioned and further processed with appropriate soft- and/or hardware.

In a preferred embodiment of the apparatus of the invention, the measuring electronics is implemented on an FPGA chip or on a dynamically reconfigurable FPGA chip or on an ASIC or on a memory chip. Moreover, it is provided that the control/evaluating/calculating unit is implemented on an FPGA chip or on a dynamically reconfigurable FPGA chip or on an ASIC or on a memory chip.

If a dynamically reconfigurable FPGA chip is used, then, for example, the functional soft- and/or hardware components can be configured in real time for the measuring unit, which is just delivering the raw measurement signals. In this way, the control/evaluating/calculating unit is, in high measure, flexibly adaptable to the respective requirements.

Furthermore, it is advantageous in connection with the apparatus of the invention when, in the case of application of a dynamically reconfigurable FPGA chip, a permanently configured region is provided, in which a microprocessor is permanently configured.

Preferably, the control/evaluating/calculating unit is implemented in a handheld device or computer or—generally stated—in a transportable service unit. For example, a smart phone or a smart pad or other transportable service unit can be used. Preferably, the software for the control/evaluating/calculating unit is downloaded from a server, as a function of the respective measuring unit, as apps, respectively as an application oriented, software unit. The server is, for example, made available by the device manufacturer. This solution has the advantage that always the current version of the software is available to the control/evaluating/calculating unit.

Preferably, the server is, moreover, a web server, so that the accessing can occur via the browser of a computer. Of course, the server can, however, be any server. Thus, also an OPC-US server can be applied.

In an especially advantageous embodiment of the apparatus of the invention, the sensor element is embodied as a laser absorption spectrometer. Preferably, the sensor element is composed of at least one wavelength-variable laser and at least one detection system. The sensor element ascertains, by means of measuring at least one absorption line of the absorption spectrum, the composition and/or the concentration of the gases.

Absorption spectroscopy with variable laser diodes (TDLAS—Tunable Diode Laser Absorption Spectroscopy) is a very sensitive and very selective method for gas analysis, respectively gas concentration measurement. In such case, a narrowband emitting laser diode enables, according to the measuring principle of one-line spectroscopy, the registering of individual absorption lines of molecular gases, such as e.g. methane (CHx), steam ($H_2O$), carbon dioxide ($CO_2$), oxygen ($O_2$), carbon monoxide (CO), and many additional gas molecules. By limiting to a very narrow bandwidth and adjustable light source, cross-sensitivity to other gases is eliminated. By means of the light absorption measurement of the gas in a defined measuring chamber, a determining of present volume concentration even in the case of very small concentrations is possible. In process measurements technology, such measuring devices are applied for gas analysis in many different applications. Most gas molecules have in the infrared spectral range of, for instance, 2 to 20 µm marked oscillation-rotation absorption lines, which can be applied for selective and quantitative detection of very small concentrations of the corresponding gas. For performing such highly accurate gas concentration measurements, a sufficient accuracy of measurement requires narrowband, monochromatic light sources having a large range of variation of wavelength. Such light sources working in the infrared spectral range are available as laser light sources in different forms of embodiment. These spectrometers with variable light sources use, for example, DFB (Distributed Feedback) laser diodes or VCSEL (Vertical Cavity Surface Emitting Laser) or a quantum cascade laser. They work, for example, in the near infrared-spectral range of 0.78 µm and 3 µm. Applied as detector units are, for example, broadband infrared receiving diodes or receiving transistors.

A basic construction of the apparatus for determining gas concentration is composed of at least one variable diode laser-light source, a so-called TDLAS, a light beam forming, radiating, reflection and receiving optics, a measuring chamber with the absorption medium, a receiving optics and at least one detector. The emission wavelength of the tunable diode laser, which, for example, is embodied in a form such as VCSEL or DEB, etc., is matched to the characteristic absorption line of the gas molecule to be evaluated in the measuring chamber, respectively cuvette. There are different constructional systems of variable diode lasers, which are selected corresponding to the application and range. Typical constructional systems include InGaAsP/InP-lasers, which are variable from 900 nm to 1.6 µm, InGaAsP/InAsP-lasers, which are variable from 1.6 µm to 2.2 µm.

The fundamental principle behind the TDLAS technology rests on determining individual absorption lines of the gases in the absorption spectrum. In such case, a diode laser radiates light in a very narrowband wavelength range into the measuring chamber, and a detection unit measures the intensity of the transmitted radiation. Thereafter, the average wavelength of the narrowband wavelength light is cyclically changed and radiated into the measuring chamber. Thus, in a certain wavelength range an absorption line of the gas located in the measuring chamber is excited and ascertained. The intensity of the transmitted radiation in the cyclically ascertained spectrum is, in such case, related to the concentration of the excited gas molecules according to the Lambert-Beer law.

As already described, integrated in the measuring unit are only functional components necessarily required on-site for the measured value registering. In the case of a laser absorption spectrometer, this involves a simple measuring unit, which has as sensor element the wavelength-variable laser and a detection system, and the measuring electronics, which registers the raw data as measured variable and sends such via an interface to the removed control/evaluation unit. The extraction, evaluation and analysis of the raw data occurs in a removed, possibly widely remote, control/evaluating unit. Conditioning- and further processing functions, same as in- and output functions, are executed only in the "central" control/evaluating/calculating unit, which obtains the therefor required, measured variables from the measuring units via an interface. The interface is embodied, for example, as an Ethernet interface, so that the control/evaluation unit can download the measured variables of the measuring unit via the Internet, respectively from a Web server. The control/evaluating/calculating unit is preferably so embodied that raw data delivered from the most varied of measuring units can be conditioned and further processed with appropriate soft- and/or hardware. Advantageously, the control/evaluating unit is integrated in a "cloud computing"-application, so that the evaluating algorithms, the measured variables of the individual measuring units and/or the parameter data of the field devices are distributed to a plurality of computers, respectively servers, connected via the Internet. The data, respectively measured variables, of the measuring units are transmitted by wire or wirelessly in real time via the corresponding interfaces, e.g. the Internet, to the computer, respectively server, of the "cloud computing" application and can be queried there. The terminology "cloud computing" means the outsourcing of applications, data, care of data and calculational procedures to the Internet, respectively the World Wide Web.

With regard to the system of the invention, the object is achieved by features including that a plurality of measuring units are connected with the control/evaluating/calculating unit via suitable communication connections. The control/evaluating/calculating unit processes the raw, measured values delivered from the different measuring units further by using the corresponding evaluating hardware and/or evaluating software and determines, improves and/or monitors the corresponding process variable, concerning which the measuring unit is to deliver information.

The system of the invention includes, among other things, elements of a computer network. Included in this network are measuring devices 1 for process variables, such as was already described above. Through the solution of the invention, the customer does not need on-site display infrastructure, thus the so-called HMI (Human Machine Interface), nor does it need the corresponding infrastructure concerning in- and outputs. Besides the on-site infrastructure for the hardware, moreover, also the on-site infrastructure for the software can be omitted. This means considerable savings.

The networking of the individual system components occurs advantageously via suitable communication connections. The communication connections include wired connections or wireless connections. Preferably used in the system of the invention are already present network infrastructures, thus especially Internet or intranet structures. Thus, the control/evaluating/calculating unit, which, among other things, provides the information concerning the process variable by application of suitable algorithms, can be part of a usual PC or laptop. Since corresponding PCs and laptops are available worldwide, the information delivered from the measuring units and then further processed is, in principle, available at any site at any time. The same holds for the in/output unit, since any PC or laptop as well as any handheld device comes equipped with display and with input means.

Furthermore, by means of the control/evaluating/calculating unit, for example, an alarm management based on diagnostic programs for the individual measuring units or parts of the system of the invention, or the configuring or parametering of the measuring units and/or of the system can be performed. Of course, responsibilities for the aforesaid functionalities can also be distributed to a number of control/evaluating/calculating units, which can be at different locations. Likewise an option is to link the information delivered from different measuring units in desired manner, in order to generate added value for the customers or also the device manufacturer.

Thus, according to the invention, a transmitter, which is associated physically with a given measuring unit, can become a virtual transmitter, which is also quite able to supplement a plurality, and even a large number, of measuring units in desired type and manner. Moreover, an option is to access the measuring units from quite different locations. This means that, in given cases, measures for assuring authorized accessing of the measuring units or the system must be included. The same holds as regards the safety of the data transmission.

Especially advantageous is, moreover, when a database is provided, in which a plurality of data sets with raw, measured values of different measuring units and/or with further processed, raw, measured values of different measuring units are stored, wherein the data sets reflect raw, measured values and/or further processed, raw, measured values, which have been ascertained as a function of different process- and/or device conditions in different applications directly or by simulation. Associated with each data set with raw, measured values and/or further processed, raw, measured values is a parameter set, which provides an optimized adjusting of the corresponding measuring unit and/or the control/evaluating/calculating unit as a function of defined process- and/or device conditions. For example, the parameters can be filter settings.

As already mentioned above, it is, moreover, provided that an added value in the form of an enrichment of information, know how and/or measurement data is provided for the user. This added value rests on the information delivered from, in given cases, different transportable service units based on the software for the control/evaluating/calculating unit. In such case, the information is normally referenced to the individual measuring units and is simultaneously available in real time. Installed in the control/evaluating/calculating unit, or units, are corresponding apps, respectively application oriented, software tools.

Alternatively, the control/evaluating/calculating unit, or units is/are installed in at least one computer. The accessing occurs then, for example, via Java or HTML. Furthermore, it is provided that the at least one control/evaluating/calculating unit obtains the suitable software from a server via web services.

As already mentioned above, it is especially advantageous in connection with the solution of the invention, when the virtual transmitter, thus the control/evaluating/calculating unit, is implemented on an iPhone, an iPad or other handheld computer.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
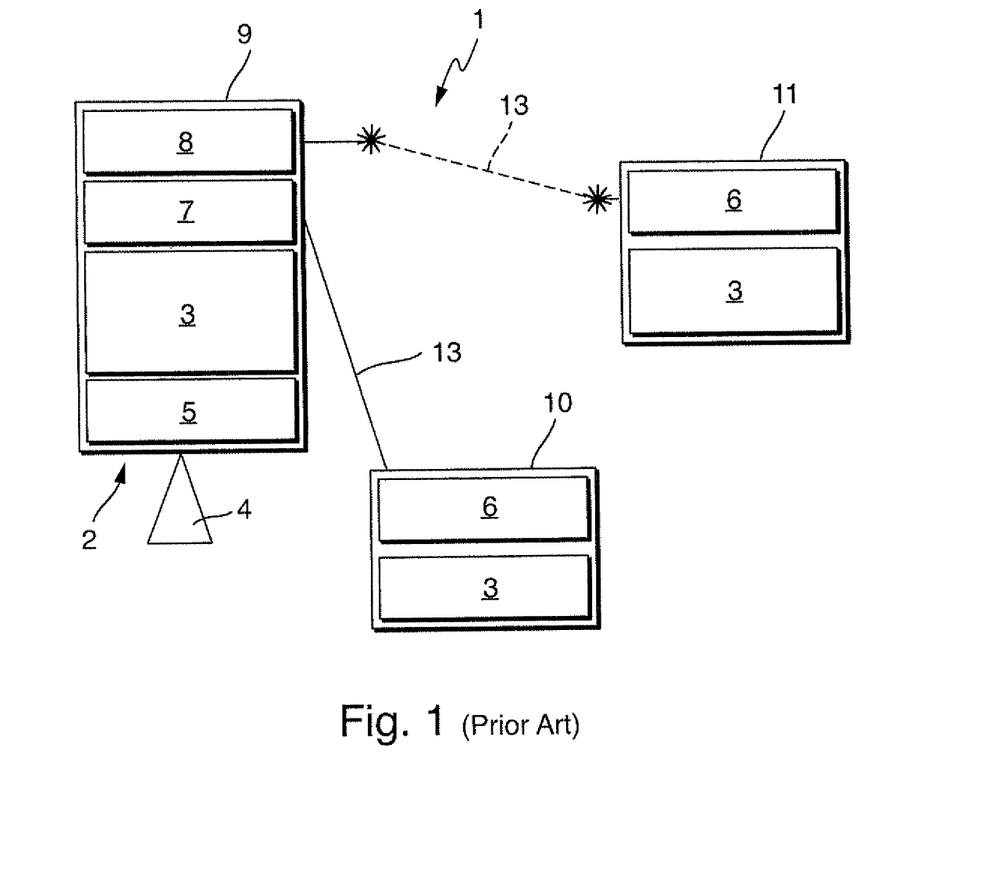
FIG. 1 is a schematic representation of a measuring apparatus known from the state of the art.

FIG. 1 shows a schematic representation of a measuring apparatus 1, such as known from the state of the art. Measuring apparatus 1 is composed of a sensor element 4, which is so embodied that it can determine a desired physical, chemical or biological process variable, and a transmitter 9, which in the shown case includes a measuring electronics 5, a control/evaluating/calculating unit 3, a first interface 7 and a second interface 8. Via the interfaces 7, 8, transmitter 9 is connected with a local service unit, for example, a handheld device 10. Furthermore, a control/evaluating/calculating unit 3 is associated with the handheld device 10 in the illustrated case. Often, the local service unit 10 in the case of known solutions is an integral component of the measuring apparatus 1.

Via the second interface 8, the transmitter 9 is connected with a remotely arranged computer 11. Associated with the computer 11 is—same as in the case of the handheld device 10—an in/output unit 6 and a control/evaluating/calculating unit. The communication connection 13 between the transmitter 9 and the local service unit 10, respectively the computer 11, occurs either wired or wirelessly, e.g. via wireless HART, for instance, one of the fieldbusses (HART, Fieldbus Foundation, Profibus, etc.) established in automation technology.

Figure 2:
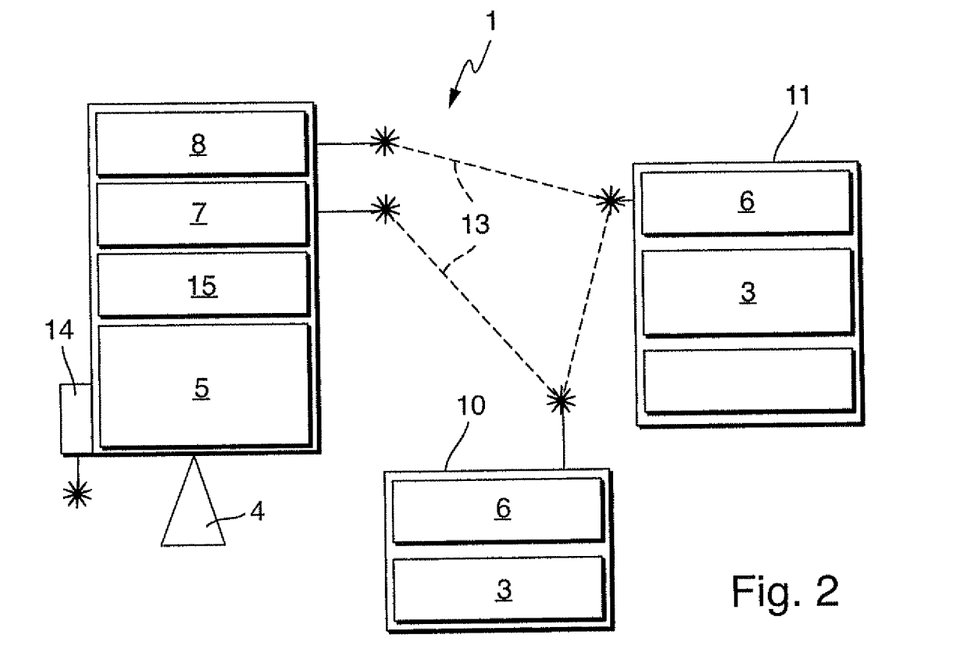
FIG. 2 is a schematic representation of a preferred embodiment of the measuring apparatus of the invention.

FIG. 2 shows a schematic representation of a preferred embodiment of the measuring apparatus 1 of the invention for determining, optimizing or monitoring at least one process variable.

Measuring apparatus 1 includes a sensor element 4 and a measuring electronics 5. Both together form the measuring unit 2, respectively the measuring module 2. The control/evaluating/calculating unit 3 is arranged removed from the measuring unit 2 and/or the in/output unit is arranged removed from the measuring unit 2 and, in given cases, from the control/evaluating/calculating unit 3. Communication between the measuring electronics 5, respectively the measuring apparatus 1, and the control/evaluating/calculating unit 3 and/or the in/output unit 6 occurs via the interfaces 7, 8. Measuring electronics 5 operates the sensor element 4 such that the measurement signals present as raw, measured values and representing the process variable are forwarded via the interfaces 7, 8 to the control/evaluating/calculating unit 3. Only in the control/evaluating/calculating unit 3 arranged removed from the measuring unit 2 is the corresponding process variable determined, improved and/or monitored based on the raw, measured values. Information concerning the process variable is made available via the in/output unit 6.

As already mentioned above, the measuring electronics 5 is implemented, for example, on an FPGA chip, a dynamically reconfigurable FPGA chip, an ASIC or a memory chip. Likewise the control/evaluating/calculating unit 3 can be implemented on an FPGA chip, a dynamically reconfigurable FPGA chip, an ASIC or a memory chip.

From corresponding applications of Endress+Hauser, it is already known that, in the case of application of a dynamically reconfigurable FPGA chips, a permanently configured region is provided, in which a microprocessor is permanently configured.

Control/evaluating/calculating unit 3 can be installed both in a manually operated device 10 as well as also in a computer 11. In general, the control/evaluating/calculating unit 3 can be located in any transportable service unit. The handheld device 10 can be, for example, a laptop, an iPhone or an iPad. The computer 11 can be e.g. a PC or an iPad. In such case, it is especially advantageous when the software for the control/evaluating/calculating unit 3 is downloadable from a server 12 as an app or as an application oriented, software unit as a function of the measuring unit 2 being used. In this way, it is assured that always the current version of the software is available. The identification of the measuring apparatus 1, respectively the measuring electronics 4, occurs e.g. via an RF-ID tag.

Figure 3:
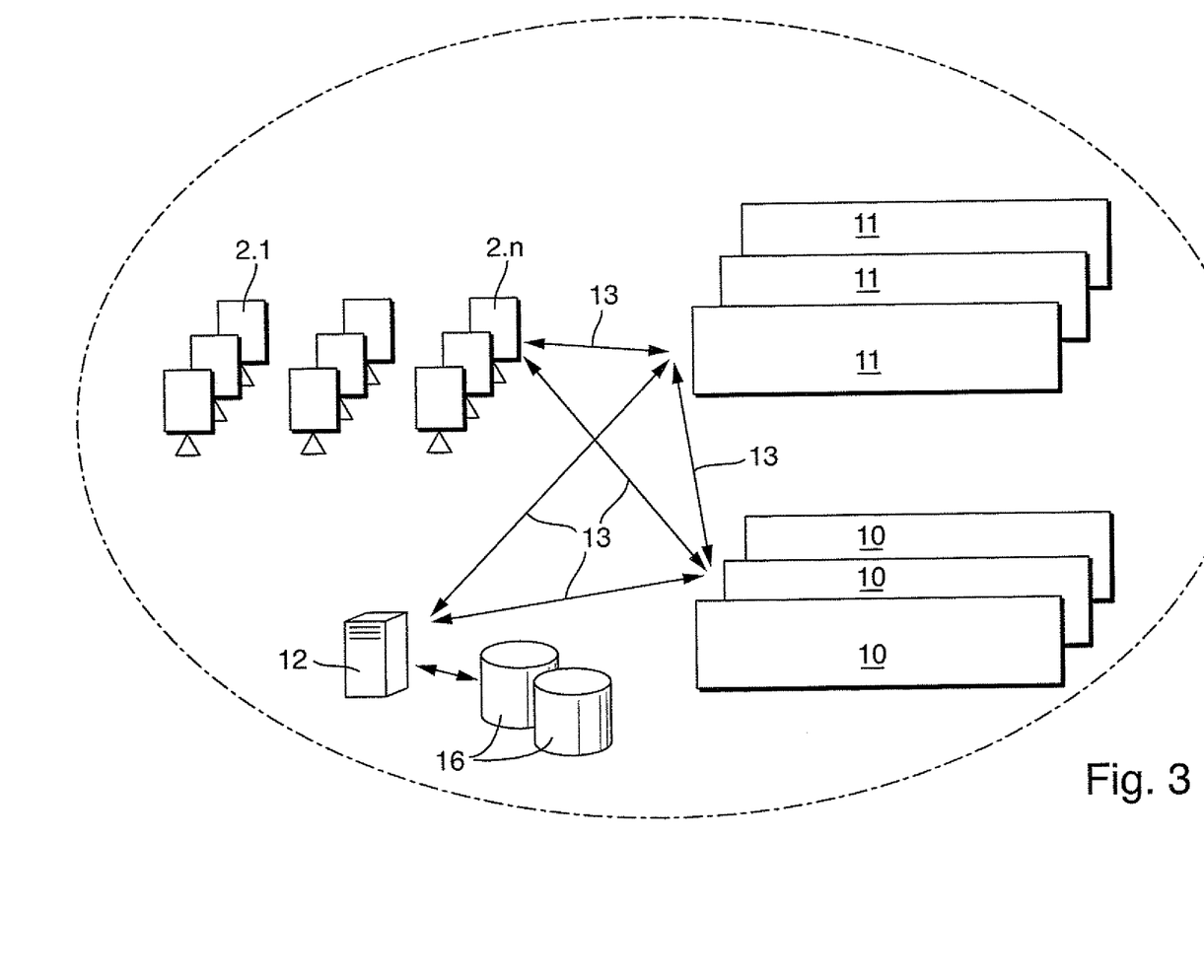
FIG. 3 is a schematic representation of an advantageous embodiment of the system of the invention.

FIG. 3 shows a schematic representation of an advantageous embodiment of the system of the invention, in the case of which a plurality of the measuring units 2.1, . . . , 2.$n$ described with respect to FIG. 2 transmit their raw, measured values to one or a few remotely arranged control/evaluation unit/s. The measuring units 2.1, . . . , 2.$n$ are, for example, integrated in an automated plant; they can, however, likewise be arranged at remote locations far from one another. Wireless communication connections 13 are preferably utilized for the purpose of data exchange. Using the corresponding evaluating hardware and/or evaluating software, the control/evaluating/calculating unit 3, which is associated either with a handheld device 10 or a computer 11, processes the raw, measured values delivered from the different measuring units 2.1, . . . , 2.$n$ and determines, improves and/or monitors the corresponding process variable.

Via a server 12, which is preferably a web server (this is advantageous, since thereby the widely distributed computer infrastructures can be utilized), the current evaluation software can be downloaded.

Furthermore, at least one database 16 is provided, in which a plurality of data sets with raw, measured values of the different measuring units 2.1, . . . , 2.$n$ and/or with further processed, raw, measured values of the different measuring units (2.1, . . . , 2.$n$) are stored, wherein the data sets reflect raw, measured values and/or further processed, raw, measured values, which have been ascertained as a function of different process- and/or device conditions in different applications directly or by simulation. Preferably there is associated with each data set with raw, measured values and/or further processed, raw, measured values a parameter set, which reflects an optimized adjusting of the corresponding measuring unit 2.1, . . . , 2.$n$ and/or the control/evaluating/calculating unit 3 as a function of the defined process- and/or device conditions. Further information for this solution is set forth in the not pre-published German patent application DE 10 2010 044 182.1 of the assignee. The corresponding passages are an integral part of the present application.

Moreover, the system of the invention provides the opportunity of achieving added value in the form of enrichment of information, know how and measurement data. The added value rests on the information delivered from the transportable service units 10, 11 based on the software for the control/evaluating/calculating unit 3 as a function of the individual measuring units 2.1, . . . , 2.$n$ units, on which the apps, respectively the application oriented software, work.

This added value can exist, for example, in the performing of advanced diagnostic functions. Furthermore, an optimizing of the energy consumption in the automated plant can represent an important added value for the user, respectively plant operator. Maintenance information represents important information for the device manufacturer and the plant operator.

Figure 4:
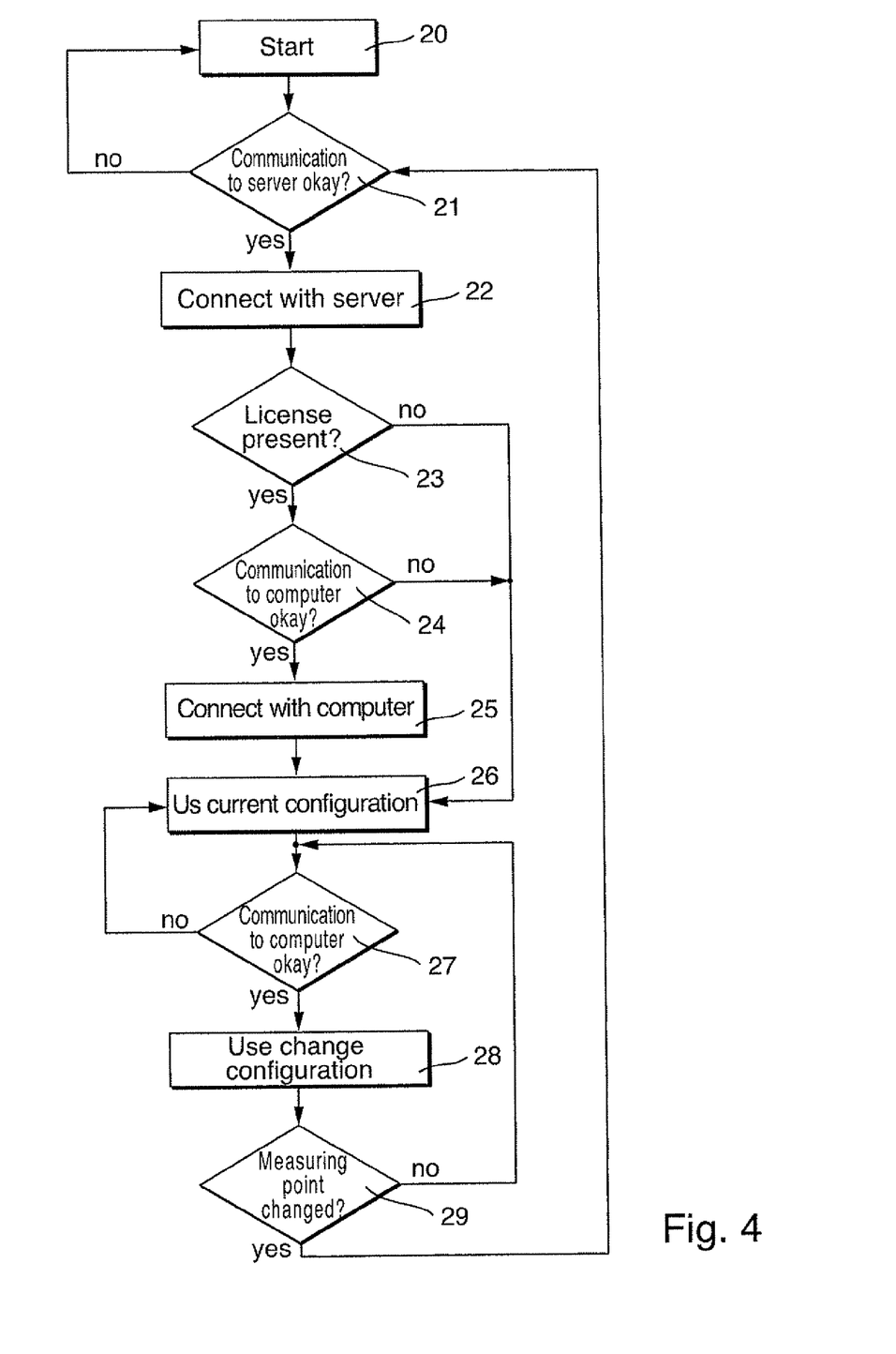
FIG. 4 is a flow diagram of a method for changing the configuration of the measuring apparatus of the invention.

FIG. 4 shows a flow diagram, which illustrates a preferred method for changing the configuration data set for the measuring electronics 5 of the measuring apparatus 1 of the invention.

The program starts at program point 20. At program point 21, it is checked whether the communication connection to the server 12, here a license server, is in order. As soon as the communication connection is established (program point 22), it is checked at the program point 23 whether authorization for accessing the license server 12 exists. For example, is the license and/or the number of the downloadable configuration data sets for the measuring electronics 5 of the measuring apparatus 1 associated with the serial number of the measuring apparatus 1? Of course, the license can also be granted with reference to the user. The license is preferably granted, in each case, for a certain number of accesses to the license server 12. So long as the maximum number of allowed accesses is not exceeded, an attempt is made to establish the connection to the computer 11, which is preferably a configuration server 11. These steps appear at program points 24, 25.

If the maximum number of allowed, licensed accesses is exceeded, then the measuring apparatus 1 works further with the current configuration of the measuring electronics 5 associated with the measuring apparatus 1 so far, until a corresponding license is present (program point 26). For the case, in which communication connection to the configuration server 11 cannot be established, the measuring apparatus 1 likewise operates further with the present configuration data set. This step appears at program point 27.

If the communication connection to the configuration server 11 can be produced, then at program point 28 a changed configuration data set is downloaded for the measuring electronics 5 from the configuration server 11 and then utilized for operating the measuring apparatus 1. The configuration data set serves, for example, for programming the FPGA chips. As soon as the measuring apparatus 1 is to be utilized for a changed measuring point (e.g. pressure measuring point instead of a fill level measuring point), the program jumps back to the program point 21. If at program point 29 no change of the measuring point is needed, then the program jumps back to the program point 27.

The invention claimed is:

1. A system comprising:
   a plurality of apparatuses, each comprising: a sensor element and a measuring electronics, which form a measuring unit;
   at least one calculating unit arranged removed from said measuring unit;
   an input/output unit arranged removed from said measuring unit and said calculating unit; and
   a database, wherein: said calculating unit and said input/output unit are connected with said measuring unit via a first interface, and a second interface;
   said measuring electronics operates said sensor element and forwards the measurement signals via said interfaces to said calculating unit as unprocessed raw data, said, calculating unit arranged removed from said measuring unit determines, improves monitors the process variable based on the raw data, and makes such available via said input/output unit; and the process variable is at least one gas composition or gas concentration;
   a plurality of measuring units are connected with said calculating unit via corresponding communication connections; and
   said calculating unit, using corresponding evaluating hardware or evaluating software, further processes raw data, delivered from the different measuring units and determines, improves monitors the corresponding process variable, and
   a plurality of data sets with the raw data of different measuring units with further processed raw data of the different measuring units are stored in said database, said data sets reflect the raw data or further processed raw data, which have been ascertained as a function of different process and device conditions in different applications directly or by simulation, and associated with each data set with the raw data or further processed raw data is a parameter set, which provides an optimized adjusting of said corresponding measuring unit said calculating unit as a function of defined process and device conditions.

2. The system as claimed in claim 1, wherein:
   said communication connections are wired connections and/or wireless connections.

3. The system as claimed in claim 1, wherein:
   added value is achieved in the form of an enrichment of information, know how and measurement data;
   the added value rests on the information delivered from transportable service units based on the software for said calculating unit as a function of said individual measuring units, in which the apps, respectively the application oriented, software units, work.

4. The system as claimed in claim 1, wherein the parameter set comprises filter settings.

* * * * *